United States Patent
Sheng et al.

(10) Patent No.: US 11,299,499 B2
(45) Date of Patent: Apr. 12, 2022

(54) PREPARATION METHOD AND APPLICATION OF ISOXAZINONE COMPOUNDS

(71) Applicant: ZHEJIANG ZHUJI UNITED CHEMICALS CO., LTD., Zhejiang (CN)

(72) Inventors: Qiuju Sheng, Zhejiang (CN); Baochuan Guan, Zhejiang (CN); Tianhao Zhang, Zhejiang (CN); Pan Zhang, Zhejiang (CN); Jinlong Zhang, Zhejiang (CN); Bangchi Chen, Zhejiang (CN)

(73) Assignee: ZHEJIANG ZHUJI UNITED CHEMICALS CO., LTD., Hangzhou (CN)

( * ) Notice: Subject to any disclaimer, the term of this patent is extended or adjusted under 35 U.S.C. 154(b) by 64 days.

(21) Appl. No.: 16/695,041

(22) Filed: Nov. 25, 2019

(65) Prior Publication Data

US 2020/0109152 A1    Apr. 9, 2020

Related U.S. Application Data

(63) Continuation of application No. PCT/CN2018/084009, filed on Apr. 23, 2018.

(30) Foreign Application Priority Data

May 26, 2017 (CN) .......................... 201710387000.5

(51) Int. Cl.
| | | |
|---|---|---|
| *C07D 498/04* | (2006.01) | |
| *C07D 309/34* | (2006.01) | |
| *C07D 401/04* | (2006.01) | |
| *C07D 413/04* | (2006.01) | |
| *C07D 413/14* | (2006.01) | |

(52) U.S. Cl.
CPC ......... *C07D 498/04* (2013.01); *C07D 309/34* (2013.01); *C07D 401/04* (2013.01); *C07D 413/04* (2013.01); *C07D 413/14* (2013.01)

(58) Field of Classification Search
CPC .. C07D 401/04; C07D 413/14; C07D 413/04; C07D 498/04
See application file for complete search history.

(56) References Cited

U.S. PATENT DOCUMENTS

| 4,446,262 A | 5/1984 | Okumura et al. |
| 4,832,897 A | 5/1989 | van der Molen |
| 8,927,559 B2 | 1/2015 | Aslanian et al. |

FOREIGN PATENT DOCUMENTS

| CN | 101535304 A | 9/2009 |
| CN | 101809006 A | 8/2010 |
| CN | 102725275 A | 10/2012 |
| CN | 102827145 A | 12/2012 |
| CN | 103058993 A | 4/2013 |
| CN | 103304508 A | 9/2013 |
| CN | 107033135 A | 8/2017 |
| CN | 107089970 A | 8/2017 |
| WO | 2003015519 A1 | 2/2003 |
| WO | 2004067528 A1 | 8/2004 |

OTHER PUBLICATIONS

PENG. Chemical Century Journal, 2017, 11:109, 1-9 (Year: 2017).*
Marko Krivec et al.;"Regioselective Hydrolysis and Transesterification of Dimethyl 3-Benzamidophthalates Assisted by a neighboring Amide Group"; J. Org. Chem.;Jun. 9, 2016; p. 5732-5739; vol. 81.
Proisl, K. et al.;;"Fischer indolisation of N-(α-ketoacyl)anthranilic acids into 2-(indol-2-carboxamido)benzoic acids and 2-indolyl-3,1-benzoxazin-4-ones and their NMR study"; Organic & Biomolecular Chemistry; Dec. 31, 2014; p. 9650-9664.
Ulrich Rose ;"2-Aryl-Substituted 4H-3,1-Benzoxazin-4-ones as Novel Active Substances for the Cardiovascular System"; J. Heterocyclic Chem.;Dec. 31, 1991; p. 2005-2012; vol. 28,No 8.

* cited by examiner

*Primary Examiner* — Noble E Jarrell

(57) ABSTRACT

Disclosed herein are a preparation method and an application of an isoxazinone compound (I), where the preparation method includes: reacting compound (II) with a carboxylic acid (III) in the presence of a dehydrating agent and a base to produce the isoxazinone compound (I); and subjecting the isoxazinone compound (I) and a protonic acid salt of an amino compound (IV) or $R_3OH$ (VII) to ring-opening reaction in the presence of a base to produce a bisamide compound (V) or an N-acyl benzoate compound (VI).

20 Claims, No Drawings

PREPARATION METHOD AND APPLICATION OF ISOXAZINONE COMPOUNDS

CROSS-REFERENCE TO RELATED APPLICATIONS

This application is a continuation of International Patent Application No. PCT/CN2018/084009, filed on Apr. 23, 2018, which claims the benefit of priority from Chinese Patent Application No. 201710387000.5, filed on May 26, 2017. The content of the aforementioned application, including any intervening amendments thereto, is incorporated herein by reference.

TECHNICAL FIELD

This application relates to organic synthesis, and more specifically to a preparation method and an application of isoxazinone compounds.

BACKGROUND

Isoxazinones (I) are an important class of compounds or intermediates in the organic synthesis and widely used in the fields of chemical engineering, pharmaceutical, pesticide, material and etc. For example, such compounds can be used respectively as a UV absorber in various UV-blocking materials (U.S. Pat. No. 4,446,262A), as a serine hydrolase inhibitor in the treatment, prevention and amelioration of serine hydrolase-mediated diseases (CN101535304A), and also used as an important intermediate in the preparation of anthranilamide insecticides (such as chlorantraniliprole and cyantraniliprole) (WO2003/015519 and WO2004/067528).

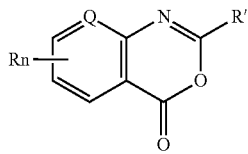

(I)

Currently, there are mainly three methods for synthesizing the isoxazinone compounds, which are described as follows.

In method 1, a carboxylic acid (III) is converted into an acyl chloride (IV) in the presence of thionyl chloride and pyridine, and then the acyl chloride (IV) is reacted with a substituted anthranilic acid (II') in the presence of a base to produce benzoxazinone (I') (U.S. Pat. No. 4,832,897 A). The reaction scheme is shown as follows:

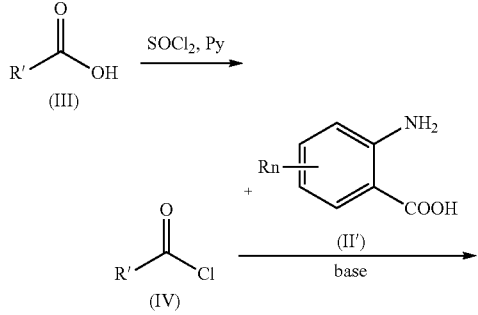

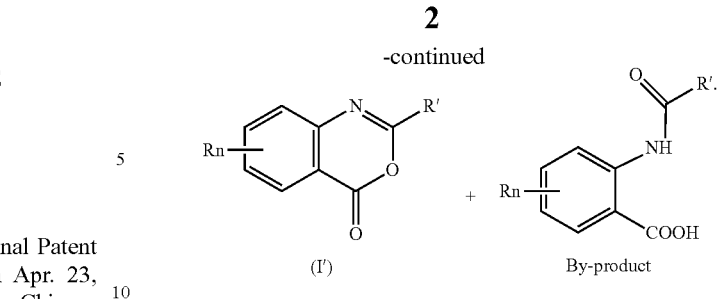

This method needs to be performed in two separate steps. Moreover, there are many byproducts formed in the reactions (U.S. Pat. No. 8,927,559 B2). This method is low yielding, not suitable for industrial production.

In method 2, a substituted anthranilic acid (II') is reacted with a carboxylic acid (III) in the presence of sulfonyl chloride and a base to directly produce benzoxazinone (I') (WO 2003/015519), the reaction scheme is shown as follows:

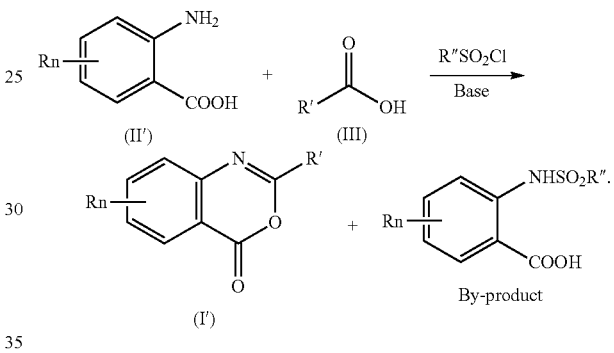

Although method 2 is simpler than method 1 and can be implemented in "one-pot" manner, this method requires excessive use of sulfonyl chloride. Sulfonyl chloride will not only react with the anthranilic acid compound to produce a large amount of sulfonamide by-product, but also will produce a considerable number of sulfur-containing organic acids in wastewater, which brings serious pollution problems. Therefore, method 2 is not suitable for industrial production either.

In method 3, a carboxylic acid (III) is first activated in the presence of an activator N,N'-carbonyldiimidazole (CDI), and then reacted with a substituted anthranilic acid (II') to produce benzoxazinone (I') (CN 101535304 A), the reaction scheme is shown as follows:

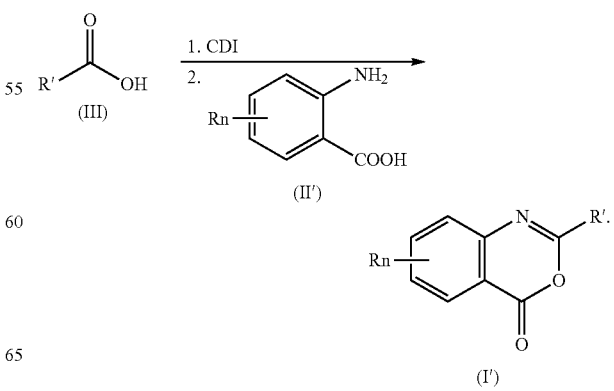

Though this method is also performed in "one-pot" manner, it requires an equivalent amount of the expensive activator N, N'-carbonyldiimidazole (CDI). The activator is very costly. In addition, the 2 equivalents of imidazole formed are not easy to recycle, causing pollution problems, making this method not suitable for industrial production.

SUMMARY

This application provides a method for preparing isoxazinone compounds (I) to overcome the drawbacks in the prior art, which has simple operation, environmentally-friendly process, low cost of raw materials, high yield and good product quality.

In a first aspect, this application provides a method for preparing an isoxazinone compound (I), comprising:

reacting compound (II) with a carboxylic acid (III) in the presence of a dehydrating agent and a base to produce the isoxazinone compound (I), as shown in the following reaction scheme:

wherein:

Q is N or C—Z;

when Q is C—Z, the compound (II) has the following structural formula:

each R and Z are independently hydrogen, alkyl, substituted alkyl, aryl, substituted aryl, heteroaryl, substituted heteroaryl, cyano, carbonyl, alkoxycarbonyl, halogen, alkoxy, alkylthio, sulfonyl, sulfinyl, alkylamino or nitro;

n is 0, 1, 2 or 3; and

R' is hydrogen, alkyl, substituted alkyl, aryl, substituted aryl, heteroaryl or substituted heteroaryl.

The substituted alkyl, aryl and heteroaryl are formed by substituting one or more hydrogen atoms on corresponding alkyl, aryl and heteroaryl each independently with alkyl, alkenyl, alkynyl, aryl, alkoxy, halogen, nitro, cyano, sulfonyl or sulfinyl.

The alkyl is a linear alkyl, a branched alkyl or a cycloalkyl.

The dehydrating agent is preferably a phosphorus reagent, where the phosphorus reagent refers to a phosphorus-containing compound and is preferably phosphorus pentoxide, phosphorus oxychloride, phosphorus oxybromide, phosphorus trichloride, phosphorus tribromide, phosphorus pentachloride or phosphorus pentabromide, and more preferably phosphorus oxychloride or phosphorus oxybromide.

The base is an inorganic base or an organic base, preferably the organic base, and more preferably a tertiary amine base, such as pyridine, triethylamine, 3-methylpyridine and N,N-dimethylaminopyridine.

A molar ratio of compound (II) to the carboxylic acid (III) is 1:0.5-1.5; a molar ratio of the compound (II) to the dehydrating agent is 1:1-2; and a molar ratio of the compound (II) to the base is 1:2-5.

In a second aspect, this application provides a method for preparing a bisamide compound (V), comprising:

subjecting the isoxazinone compound (I) prepared by the above method and a protonic acid salt of an amino compound (IV) to ring-opening reaction in the presence of a base to produce the bisamide compound (V), as shown in the following reaction scheme:

wherein:

Q, n, R and R' are defined as above;

$R_1$ and $R_2$ are independently hydrogen, alkyl, substituted alkyl, aryl, substituted aryl, heteroaryl or substituted heteroaryl, but are not simultaneously hydrogen;

the alkyl is a linear alkyl, a branched alkyl or a cycloalkyl; and

HY is hydrohalic acid, sulfuric acid, phosphoric acid or carboxylic acid, preferably hydrochloric acid or sulfuric acid.

The base used in the ring-opening reaction is an organic base or an inorganic base, preferably the organic base, and more preferably triethylamine, pyridine, 3-methylpyridine or N,N-dimethylaminopyridine.

In a third aspect, this application provides a method for preparing an N-acyl benzoate compound (VI), comprising:

subjecting the isoxazinone compound (I) prepared by the above method and $R_3OH$ (VII) to ring-opening reaction in the presence of a base to produce the N-acyl benzoate compound (VI), as shown in the following reaction scheme:

wherein:

Q, n, R and R' are defined as above; and $R_3$ is alkyl, substituted alkyl, alkenyl, alkynyl, aryl, substituted aryl, heteroaryl or substituted heteroaryl.

The base used in the ring-opening reaction is an inorganic base or an organic base, such as an alkali metal carbonate, an alkali metal hydroxide, an alkali metal alkoxide, triethylamine and pyridine, preferably the alkali metal alkoxide, and more preferably a salt formed by $R_3OH$ and an alkali metal, such as $R_3ONa$ and $R_3OK$.

Compared to the prior art, the method provided herein for preparing an isoxazinone compound has the following beneficial effects.

(1) This method uses readily-available and cheap raw materials, and the production cost is low.

(2) This method is free of methanesulfonyl chloride, avoiding the production of organic sulfur-containing wastewater, and the waste produced is low and easily treated.

(3) This method is performed in "one-pot" manner. The operation is simple, the reaction conditions are mind, the yield is high, making the method suitable for industrial production.

DETAILED DESCRIPTION OF EMBODIMENTS

The features of the invention will be further illustrated below with reference to the embodiments, but these embodiments are not intended to limit the invention.

Example 1 Preparation of 2-[3-bromo-1-(3-chloro-2-pyridinyl)-1H-pyrazol-5-yl]-6-chloro-8-methyl-4H-3,1-benzoxazin-4-one 3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask, to which 5.73 g of $POBr_3$ was dropwise added at −5° C. The reaction mixture was stirred for half an hour with the temperature kept, and then 1.86 g of 2-amino-3-methyl-5-chlorobenzoic acid was added. The reaction mixture was reacted at room temperature for 1 h. After the reaction was complete, the reaction mixture was added with 20 mL of water, stirred for 0.5 h and filtered. The filter cake was washed with a mixture of acetonitrile and water in a ratio of 3:2 and dried to give 4.16 g of 2-[3-bromo-1-(3-chloro-2-pyridinyl)-1H-pyrazol-5-yl]-6-chloro-8-methyl-4H-3,1-benzoxazin-4-one, and the yield was 92%.

Example 2 Preparation of 2-[3-bromo-1-(3-chloro-2-pyridinyl)-1H-pyrazol-5-yl]-6-cyano-8-methyl-4H-3,1-benzoxazin-4-one 3.02 g of 3-bromo-1-(3-chloro-2-pyridinyl)-1H-pyrazole-5-carboxylic acid, 1.95 g of 3-methylpyridine and 15 mL of acetonitrile were added to a 100 mL three-necked flask, to which 3.23 g of $POCl_3$ was dropwise added at −5° C. The reaction mixture was stirred for half an hour with the temperature kept, and then 1.94 g of 2-amino-3-methyl-5-cyanobenzoic acid was added. The reaction mixture was reacted at room temperature for 1 h. After the reaction was complete, the reaction mixture was added with 20 mL of water, stirred for 0.5 h and filtered. The filter cake was washed with a mixture of acetonitrile and water in a ratio of 3:2 and dried to give 3.82 g of 2-[3-bromo-1-(3-chloro-2-pyridinyl)-1H-pyrazol-5-yl]-6-cyano-8-methyl-4H-3,1-ben zoxazin-4-one, and the yield was 86%.

$^1$H NMR (500 MHz, DMSO): δ 8.63 (dd, 1H), 8.40-8.33 (m, 2H), 8.10 (s, 1H), 7.77 (dd, 1H), 7.60 (s, 1H), 1.73 (s, 3H).

Example 3 Preparation of 2-[3-bromo-1-(3-chloro-2-pyridinyl)-1H-pyrazol-5-yl]-8-methyl-4H-3,1-benzoxazin-4-one 3.02 g of 3-bromo-1-(3-chloro-2-pyridinyl)-1H-pyrazole-5-carboxylic acid, 2.02 g of triethylamine and 15 mL of acetonitrile were added to a 100 mL three-necked flask, to which 3.23 g of $POCl_3$ was dropwise added at −5° C. The reaction mixture was stirred for half an hour with the temperature kept, and then 3.02 g of 2-amino-3-methylbenzoic acid was added. The reaction mixture was reacted at room temperature for 2 h. After the reaction was complete, the reaction mixture was added with 20 mL of water, stirred for 0.5 h and filtered. The filter cake was washed with a mixture of acetonitrile and water in a ratio of 3:2 and dried to give 3.76 g of 2-[3-bromo-1-(3-chloro-2-pyridinyl)-1H-pyrazol-5-yl]-8-methyl-4H-3,1-benzoxazin-4-one, and the yield was 90%.

$^1$HNMR (500 MHz, DMSO): δ8.63 (dd, 1H), 8.35 (dd, 1H), 7.93 (d, 1H), 7.76 (dd, 1H), 7.68 (d, 1H), 7.49 (dd, 2H), 1.74 (s, 3H).

Example 4 Preparation of 2-[3,4-Dibromo-1-(3-chloro-2-pyridinyl)-1H-pyrazol-5-yl]-6-cyano-8-methyl-4H-3,1-benzoxazin-4-one 3.81 g of 3,4-Dibromo-1-(3-chloro-2-pyridinyl)-1H-pyrazole-5-carboxylic acid, 2.46 g of N,N-dimethylaminopyridine and 15 mL of acetonitrile were added to a 100 mL three-necked flask, to which 3.23 g of $POCl_3$ was dropwise added at −5° C. The reaction mixture was stirred for half an hour with the temperature kept, and then 1.86 g of 2-amino-3-methyl-5-chlorobenzoic acid was added. The reaction mixture was reacted at room temperature for 3 h. After the reaction was complete, the reaction mixture was added with 20 mL of water, stirred for 0.5 h and filtered. The filter cake was washed with a mixture of acetonitrile and water in a ratio of 3:2 and dried to give 5.04 g of 2-[3,4-Dibromo-1-(3-chloro-2-pyridinyl)-1H-pyrazol-5-yl]-6-cyano-8-methyl-4H-3,1-benzoxazin-4-one, and the yield was 95%.

$^1$H NMR (400 MHz, DMSO): δ8.60 (d, 1H), 8.36 (d, 1H), 7.97-7.88 (m, 1H), 7.83 (s, 1H), 7.76 (dd, 1H), 1.88 (S, 3H).

Example 5 Preparation of 2-[3-bromo-1-(3-chloro-2-pyridinyl)-1H-pyrazol-5-yl]-6-bromo-8-methyl-4H-3,1-benzoxazin-4-one 3.02 g of 3-bromo-1-(3-chloro-2-pyridinyl)-1H-pyrazole-5-carboxylic acid, 3.95 g of pyridine and 15 mL of acetonitrile were added to a 100 mL three-necked flask, to which 3.23 g of $PCl_3$ was dropwise added at −5° C. The reaction mixture was stirred for half an hour with the temperature kept, and then 2.3 g of 2-amino-3-methyl-5-bromobenzoic acid was added. The reaction mixture was reacted at room temperature for 1 h. After the reaction was complete, the reaction mixture was added with 20 mL of water, stirred for 0.5 h and filtered. The filter cake was washed with a mixture of acetonitrile and water in a ratio of 3:2 and dried to give 4.42 g of 2-[3-bromo-1-(3-chloro-2-pyridinyl)-1H-pyrazol-5-yl]-6-bromo-8-methyl-4H-3,1-ben zoxazin-4-one, and the yield was 89%.

$^1$H NMR (500 MHz, DMSO): δ8.63 (dd, 1H), 8.35 (dd, 1H), 8.02 (d, 1H), 7.95-7.87 (m, 1H), 7.77 (dd, 1H), 7.54 (s, 1H), 1.71 (s, 3H).

Example 6 Preparation of 2-[pyridin-4-yl]-6-chloro-8-methyl-4H-3,1-benzoxazin-4-one 1.84 g of isonicotinic acid, 2.02 g of triethylamine and 15 mL of acetonitrile were added to a 100 mL three-necked flask, to which 4.59 g of POCl$_3$ was dropwise added at −5° C. The reaction mixture was stirred for half an hour with the temperature kept, and then 1.86 g of 2-amino-3-methyl-5-chloromobenzoic acid was added. The reaction mixture was reacted at room temperature for 2.5 h. After the reaction was complete, the reaction mixture was added with 20 mL of water, stirred for 0.5 h and filtered. The filter cake was washed with a mixture of acetonitrile and water in a ratio of 3:2 and dried to give 2.5 g of 2-[pyridin-4-yl]-6-chloro-8-methyl-4H-3,1-benzoxazin-4-one, and the yield was 92%.

$^1$H NMR (400 MHz, DMSO): δ 8.86 (d, 2H), 8.09 (dd, 2H), 8.01-7.92 (m, 2H), 2.62 (s, 3H).

Example 7 Preparation of 2-[3-bromo-1-(3-chloro-2-pyridinyl)-1H-pyrazol-5-yl]-4H-pyrido[2,3-d][3,1]oxazin-4-one 3.02 g of 3-bromo-1-(3-chloro-2-pyridinyl)-1H-pyrazole-5-carboxylic acid, 2.02 g of triethylamine and 15 mL of acetonitrile were added to a 100 mL three-necked flask, to which 4.59 g of POCl$_3$ was dropwise added at −5° C. The reaction mixture was stirred for half an hour with the temperature kept, and then 1.86 g of 2-amino-3-picolinic acid was added. The reaction mixture was reacted at room temperature for 2 h. After the reaction was complete, the reaction mixture was added with 20 mL of water, stirred for 0.5 h and filtered. The filter cake was washed with a mixture of acetonitrile and water in a ratio of 3:2 and dried to give 3.67 g of 2-[3-bromo-1-(3-chloro-2-pyridinyl)-1H-pyrazol-5-yl]-4H-pyrido[2,3-d][3,1]oxazin-4-one, and the yield was 91%.

$^1$H NMR (400 MHz, DMSO): δ8.88 (dd, 1H), 8.63-8.56 (m, 1H), 8.52-8.43 (m, 1H), 8.33 (dd, 1H), 7.77 (dd, 1H), 7.65-7.56 (m, 2H).

Example 8 Preparation of 3-bromo-N-(2-methyl-4-cyano-6-(carbamoyl)phenyl)-1-(3-chloro-2-pyridinyl)-1H-pyrazole-5-carboxamide 4.17 g of 2-[3-bromo-1-(3-chloro-2-pyridinyl)-1H-pyrazol-5-yl]-6-cyano-8-methyl-4H-3,1-benzoxazin-4-one was dissolved in 20 mL of acetonitrile, to which 1.78 g of triethylamine and 2.82 g of methylamine sulfate were added. The reaction mixture was stirred at room temperature for 2.5 h, desolventizied under vacuum, washed with water and dried to give 4.08 g of 3-bromo-N-(2-methyl-4-cyano-6-(carbamoyl)phenyl)-1-(3-chloro-2-pyridinyl)-1H-pyrazole-5-carboxamide, and the yield was 98%.

Example 9 Preparation of 3-bromo-N-(2-methyl-4-chloro-6-(carbamoyl)phenyl)-1-(3-chloro-2-pyridinyl)-1H-pyrazole-5-carboxamide 4.2 g of 2-[3-bromo-1-(3-chloro-2-pyridinyl)-1H-pyrazol-5-yl]-6-chloro-8-methyl-4H-3,1-benzoxazin-4-one was dissolved in 20 mL of acetonitrile, to which 1.23 g of 4-dimethylaminopyridine and 2.18 g of methylamine sulfate were added. The reaction mixture was stirred at room temperature for 2.5 h, desolventizied under vacuum, washed with water and dried to give 4.27 g of 3-bromo-N-(2-methyl-4-chloro-6-(carbamoyl)phenyl)-1-(3-chloro-2-pyridinyl)-1H-pyrazole-5-carboxamide, and the yield was 95%.

Example 10 Preparation of 3-bromo-N-(2-methyl-4-chloro-6-(methoxycarbonyl)phenyl)-1-(3-chloro-2-pyridinyl)-1H-pyrazole-5-carboxamide 10 g of 2-[3-bromo-1-(3-chloro-2-pyridinyl)-1H-pyrazol-5-yl]-6-chloro-8-methyl-4H-3,1-benzoxazin-4-one was dissolved in 100 mL of methanol, to which 10 g of sodium methoxide was added at room temperature. The reaction mixture was reacted under stirring for 1 h, and then desolventizied under vacuum, washed with water and dried to give 9.74 g of 3-bromo-N-(2-methyl-4-chloro-6-(methoxycarbonyl)phenyl)-1-(3-chloro-2-pyridinyl)-1H-pyrazole-5-carboxamide, and the yield was 91%.

What is claimed is:

1. A method for preparing an isoxazinone compound (I), comprising:
reacting compound (II) with a carboxylic acid (III) in the presence of a dehydrating agent and a base to produce the isoxazinone compound (I), as shown in the following reaction scheme:

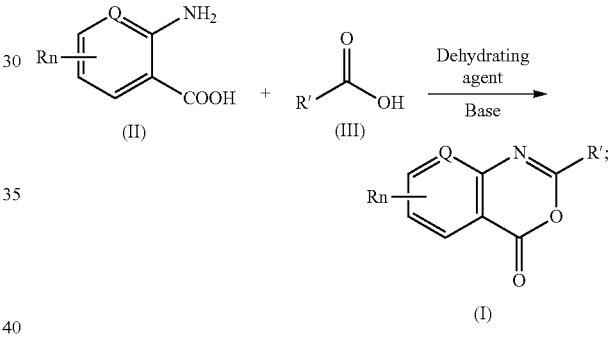

wherein:
Q is N or C—Z;
each R is independently alkyl, substituted alkyl, aryl, substituted aryl, heteroaryl, substituted heteroaryl, cyano, carbonyl, alkoxycarbonyl, halogen, alkoxy, alkylthio, sulfonyl, sulfinyl, alkylamino or nitro; each Z is independently hydrogen, alkyl, substituted alkyl, aryl, substituted aryl, heteroaryl, substituted heteroaryl, cyano, carbonyl, alkoxycarbonyl, halogen, alkoxy, alkylthio, sulfonyl, sulfinyl, alkylamino or nitro;
n is 0, 1, 2 or 3; and
R' is hydrogen, alkyl, substituted alkyl, aryl, substituted aryl, heteroaryl or substituted heteroaryl; and
the dehydrating agent is a phosphorus reagent.

2. The method of claim 1, wherein the base is an organic base.

3. The method of claim 1, wherein the phosphorus reagent is selected from the group consisting of phosphorus pentoxide, phosphorus oxychloride, phosphorus oxybromide, phosphorus trichloride, phosphorus tribromide, phosphorus pentachloride and phosphorus pentabromide.

4. The method of claim 3, wherein the phosphorus reagent is phosphorus oxychloride or phosphorus oxybromide.

5. The method of claim 2, wherein the organic base is selected from the group consisting of pyridine, 3-methylpyridine, N,N-dimethylaminopyridine and triethylamine.

6. The method of claim 1, wherein a molar ratio of the compound (II) to the carboxylic acid (III) is 1:0.5-1.5; a molar ratio of the compound (II) to the dehydrating agent is 1:1-2; and a molar ratio of the compound (II) to the base is 1:2-5.

7. A method for preparing a bisamide compound (V), comprising:
reacting compound (II) with a carboxylic acid (III) in the presence of a dehydrating agent and a first base to produce the isoxazinone compound (I); and
subjecting the isoxazinone compound (I) and a protonic acid salt of an amino compound (IV) to ring-opening reaction in the presence of a second base to produce the bisamide compound (V), as shown in the following reaction scheme:

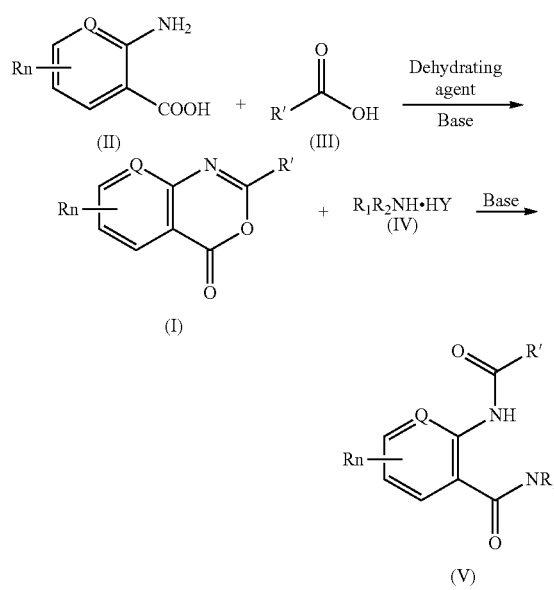

wherein:
Q is N or C—Z;
each R is independently alkyl, substituted alkyl, aryl, substituted aryl, heteroaryl, substituted heteroaryl, cyano, carbonyl, alkoxycarbonyl, halogen, alkoxy, alkylthio, sulfonyl, sulftnyl, alkylamino or nitro; each Z is independently hydrogen, alkyl, substituted alkyl, aryl, substituted aryl, heteroaryl, substituted heteroaryl, cyano, carbonyl, alkoxycarbonyl, halogen, alkoxy, alkylthio, sulfonyl, sulfinyl, alkylamino or nitro;
n is 0, 1, 2 or 3;
R' is hydrogen, alkyl, substituted alkyl, aryl, substituted aryl, heteroaryl or substituted heteroaryl;
$R_1$ and $R_2$ are independently hydrogen, alkyl, substituted alkyl, aryl, substituted aryl, heteroaryl or substituted heteroaryl, but are not simultaneously hydrogen; and
HY is hydrohalic acid, sulfuric acid, phosphoric acid or carboxylic acid.

8. The method of claim 7, wherein HY is hydrochloric acid or sulfuric acid; and the second base used in the ring-opening reaction is triethylamine, pyridine, 3-methylpyridine or N,N-dimethylaminopyridine.

9. The method of claim 7, wherein the dehydrating agent is a phosphorus reagent and the first base is an organic base.

10. The method of claim 9, wherein the phosphorus reagent is selected from the group consisting of phosphorus pentoxide, phosphorus oxychloride, phosphorus oxybromide, phosphorus trichloride, phosphorus tribromide, phosphorus pentachloride and phosphorus pentabromide.

11. The method of claim 10, wherein the phosphorus reagent is phosphorus oxychloride or phosphorus oxybromide.

12. The method of claim 9, wherein the organic base is selected from the group consisting of pyridine, 3-methylpyridine, N,N-dimethylaminopyridine and triethylamine.

13. The method of claim 7, wherein a molar ratio of the compound (II) to the carboxylic acid (III) is 1:0.5-1.5; a molar ratio of the compound (II) to the dehydrating agent is 1:1-2; and a molar ratio of the compound (II) to the first base is 1:2-5.

14. A method for preparing an N-acyl benzoate compound (VI), comprising:
reacting compound (II) with a carboxylic acid (III) in the presence of a dehydrating agent and a first base to produce the isoxazinone compound (I); and
subjecting the isoxazinone compound (I) and $R_3OH$ (VII) to ring-opening reaction in the presence of a second base to produce the N-acyl benzoate compound (VI), as shown in the following reaction scheme:

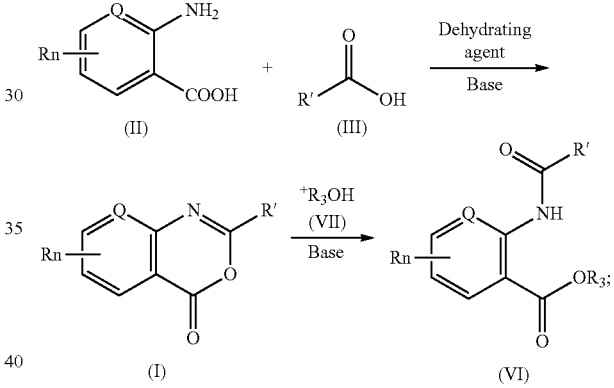

wherein:
Q is N or C—Z;
each R is independently alkyl, substituted alkyl, aryl, substituted aryl, heteroaryl, substituted heteroaryl, cyano, carbonyl, alkoxycarbonyl, halogen, alkoxy, alkylthio, sulfonyl, sulftnyl, alkylamino or nitro; each Z is independently hydrogen, alkyl, substituted alkyl, aryl, substituted aryl, heteroaryl, substituted heteroaryl, cyano, carbonyl, alkoxycarbonyl, halogen, alkoxy, alkylthio, sulfonyl, sulfinyl, alkylamino or nitro;
n is 0, 1, 2 or 3;
R' is hydrogen, alkyl, substituted alkyl, aryl, substituted aryl, heteroaryl or substituted heteroaryl; and
$R_3$ is alkyl, substituted alkyl, alkenyl, alkynyl, aryl, substituted aryl, heteroaryl or substituted heteroaryl.

15. The method of claim 14, wherein the second base used in the ring-opening reaction is an alkoxide of an alkali metal.

16. The method of claim 14, wherein the dehydrating agent is a phosphorus reagent and the first base is an organic base.

17. The method of claim 16, wherein the phosphorus reagent is selected from the group consisting of phosphorus pentoxide, phosphorus oxychloride, phosphorus oxybromide, phosphorus trichloride, phosphorus tribromide, phosphorus pentachloride and phosphorus pentabromide.

18. The method of claim 17, wherein the phosphorus reagent is phosphorus oxychloride or phosphorus oxybromide.

19. The method of claim 16, wherein the organic base is selected from the group consisting of pyridine, 3-methylpyridine, N,N-dimethylaminopyridine and triethylamine.

20. The method of claim 14, wherein a molar ratio of the compound (II) to the carboxylic acid (III) is 1:0.5-1.5; a molar ratio of the compound (II) to the dehydrating agent is 1:1-2; and a molar ratio of the compound (II) to the first base is 1:2-5.

* * * * *